US009814470B2

(12) United States Patent
Weekes et al.

(10) Patent No.: US 9,814,470 B2
(45) Date of Patent: Nov. 14, 2017

(54) OFFSET ORTHOPAEDIC REAMER HANDLE

(71) Applicant: Symmetry Medical Manufacturing, Inc., Warsaw, IN (US)

(72) Inventors: Stuart Weekes, Gloucestershire (GB); Jim Truscott, Gloucestershire (GB); Guillaume Kerboul, Gloucestershire (GB)

(73) Assignee: Symmetry Medical Manufacturing, Inc., Warsaw, IN (US)

( * ) Notice: Subject to any disclaimer, the term of this patent is extended or adjusted under 35 U.S.C. 154(b) by 571 days.

(21) Appl. No.: 14/285,176

(22) Filed: May 22, 2014

(65) Prior Publication Data
US 2015/0335335 A1 Nov. 26, 2015

(51) Int. Cl.
*F16D 3/38* (2006.01)
*A61B 17/16* (2006.01)
*A61B 17/00* (2006.01)

(52) U.S. Cl.
CPC ...... *A61B 17/1666* (2013.01); *A61B 17/1631* (2013.01); *A61B 17/1633* (2013.01); *A61B 2017/0046* (2013.01); *A61B 2017/0069* (2013.01)

(58) Field of Classification Search
CPC ........ F16C 11/06; F16D 3/38; A61B 17/1666; Y10T 403/32041; Y10T 403/32049; Y10T 403/32893
See application file for complete search history.

(56) References Cited

U.S. PATENT DOCUMENTS 4,271,849 A    6/1981  Rehder
4,365,488 A  * 12/1982  Mochida ............... F16D 3/38
                                                         403/57
(Continued)

FOREIGN PATENT DOCUMENTS

DE  20 2007 003 139 U1    7/2007
EP       2 818 126 A1    12/2014
FR       1 200 466    *   6/1958  ............... F16D 3/38

OTHER PUBLICATIONS

Extended European Search Report dated Apr. 26, 2016 for European Patent Application No. 14003583 (11 pages).
(Continued)

*Primary Examiner* — Michael P Ferguson
(74) *Attorney, Agent, or Firm* — Taylor IP, P.C.

(57) ABSTRACT

The present invention provides an orthopedic reamer handle that includes a reamer portion configured to transmit torque to a reamer head, a driver portion connected to the reamer portion that is configured to receive and transmit torque from a driver, and a drive train connecting the reamer portion to the driver portion to transmit torque from the driver portion to the reamer portion. The drive train includes a first drive shaft that defines a first axis and is connected to the driver portion at a first end and to a first intermediate connector at a second end. An offsetting member is connected to a second intermediate end of the first intermediate connector at an acute angle relative to the first axis and defines a second axis. The offsetting member connects to the reamer portion via a second intermediate connector at an acute angle relative to the second axis.

6 Claims, 6 Drawing Sheets

(56) References Cited

U.S. PATENT DOCUMENTS

| | | | |
|---|---|---|---|
| 4,371,358 A * | 2/1983 | Laue | F16D 3/40 403/58 |
| 5,062,730 A * | 11/1991 | Tomii | F16D 3/38 403/57 |
| 5,171,312 A | 12/1992 | Salyer | |
| 5,324,235 A * | 6/1994 | Tomii | F16D 1/0864 403/58 |
| 5,601,377 A * | 2/1997 | Ohya | B21D 53/00 29/417 |
| 5,817,096 A | 10/1998 | Salyer | |
| 6,875,217 B2 | 4/2005 | Wolford | |
| 7,140,969 B2 * | 11/2006 | Prucher | F16D 3/387 403/57 |
| 7,473,254 B2 | 1/2009 | White et al. | |
| 7,513,899 B2 | 4/2009 | Grim | |
| 7,572,259 B2 | 8/2009 | Desarzens et al. | |
| 7,588,572 B2 | 9/2009 | White et al. | |
| 7,608,076 B2 | 10/2009 | Ezzedine | |
| 7,637,909 B2 | 12/2009 | Lechot et al. | |
| 7,670,343 B2 | 3/2010 | Meridew et al. | |
| 7,753,612 B2 * | 7/2010 | Bouru | F16C 11/045 403/123 |
| 7,785,329 B2 | 8/2010 | Lechot et al. | |
| 7,901,405 B2 | 3/2011 | White et al. | |
| 8,052,690 B2 | 11/2011 | Berthusen et al. | |
| 8,357,163 B2 | 1/2013 | Sidebotham et al. | |
| 8,454,609 B2 | 6/2013 | Petit et al. | |
| 8,469,622 B2 * | 6/2013 | McClanahan | E02F 3/58 37/399 |
| 8,475,460 B1 | 7/2013 | Roger et al. | |
| 8,480,674 B1 | 7/2013 | Roger et al. | |
| 2002/0066329 A1 | 6/2002 | Brickner et al. | |
| 2004/0172036 A1 | 9/2004 | Dye | |
| 2005/0038443 A1 | 2/2005 | Hedley et al. | |
| 2005/0216020 A1 | 9/2005 | Orton | |
| 2007/0073302 A1 | 3/2007 | Myers et al. | |
| 2007/0142840 A1 | 6/2007 | Goodwin et al. | |
| 2008/0058804 A1 | 3/2008 | Lechot et al. | |
| 2008/0287952 A1 | 11/2008 | Mcminn et al. | |
| 2012/0087718 A1 | 4/2012 | Long | |
| 2012/0136357 A1 | 5/2012 | Torrie et al. | |
| 2013/0331841 A1 | 12/2013 | Roger et al. | |
| 2015/0005776 A1 | 1/2015 | Biegun | |

OTHER PUBLICATIONS

Extended European Search Report dated Jun. 14, 2017 for European Application No. 17 15 0598 (16 pages).

* cited by examiner

OFFSET ORTHOPAEDIC REAMER HANDLE

BACKGROUND OF THE INVENTION

1. Field of the Invention

The present invention relates to orthopaedic reamer handles, and, more particularly, to orthopaedic reamer handles with an offset.

2. Description of the Related Art

A hip replacement surgery is a common orthopaedic procedure that is performed when a patient's cartilage in the acetabulum joint of the hip has been damaged or destroyed, leading to bone-on-bone contact between the femoral head and the hip. The bone-on-bone contact leads to the formation of arthritic bone and cartilage, which must be removed prior to inserting the hip implant. To remove arthritic bone and cartilage, as well as create a good contact surface for installation of an acetabular cup, an acetabular reamer is used. Most acetabular reamers have a reamer head with a spherical shape and openings formed throughout the surface of the reamer head, much like a cheese grater. The reamer head is connected to a rotary driver, such as a drill, by a drive train within the reamer, and removes the diseased bone and cartilage as it spins within the acetabulum. Orthopaedic reamers are also used in other joints of the body, such as the glenohumeral joint.

In some acetabular reamer designs, the section of the reamer containing the drive train, referred to as a reamer handle, has an offset between the part that connects to the driver and the reamer head. The offset of the reamer handle allows for the reamer head to access the acetabulum on a different axis than the driver, which can be beneficial during surgery. An offset reamer handle requires a substantially different drive train than a straight reamer handle to transfer rotational torques from the driver to the reamer head, as well as a different casing to enclose the drive train.

One such reamer handle is described in U.S. Pat. No. 8,480,674 to Roger et al. The reamer handle described in Roger et al. has a driver portion connected to a driver, a shaft rotatably connected to the driver portion, and a joint between the shaft and a reamer head that transfers torque from the shaft to the reamer head. The joint is angled relative to the shaft to provide the offset for the reamer handle. One limitation of the reamer handle described in Roger et al. is that the length and angle of the offset is determined by the joint, lowering the design flexibility of the reamer handle. The joint connecting the shaft to the reamer head of Roger et al. also has pins that rigidly connect the shaft and reamer head to the joint, i.e., the pins don't rotate during operation, and bear little of the frictional forces that produce wear during operation.

What is needed in the art is an offset orthopaedic reamer handle that allows for more design flexibility and has better wear distribution.

SUMMARY OF THE INVENTION

The present invention provides an orthopaedic reamer handle that includes an offset formed by an offsetting member and a second intermediate connector, as well as a joint for transmitting torque through the reamer handle that includes a rotating, stepped pin.

The invention in one form is directed to an orthopaedic reamer handle that includes a reamer portion, a driver portion connected to the reamer portion, and a drive train connecting the reamer portion to the driver portion. The reamer portion is configured to transmit torque to a reamer head. The driver portion is configured to receive and transmit torque from a driver. The drive train is configured to transmit torque from the driver portion to the reamer portion and includes a first drive shaft connected to the driver portion that defines a first axis, a first intermediate connector connected to the first drive shaft, an offsetting member connected to said first intermediate connector that defines a second axis, and a second intermediate connector connected to the offsetting member and the reamer portion. The first drive shaft has a first end that is connected to the driver portion and a second end that is connected to a first intermediate end of the first intermediate connector. The first intermediate connector has a second intermediate end that connects to a third end of the offsetting member at an acute angle relative to the first axis. The second intermediate connector connects a fourth end of the offsetting member and the reamer portion at an acute angle relative to the second axis.

The invention in another form is directed to a joint for transmitting torque in an orthopaedic reamer handle that includes a first connector, a second connector connected to the first connector, a joining member connecting the first connector to the second connector, a stepped pin placed at least partly within the first connector and joining member, and a cap placed over a region of the stepped pin. The first connector includes a first ear and a second ear connected to a base and separated by a first gap. The first ear has a first pin opening with a first opening diameter and the second ear has a second pin opening with a second opening diameter. The joining member has a pair of opposing faces with a first face opening formed therethrough. The stepped pin is placed through the first pin opening, the second pin opening and the first face opening. The stepped pin has a first region with a first pin diameter that is less than the first opening diameter, a second region with a second pin diameter that is greater than the first opening diameter and less than the second opening diameter, and a third region with a third pin diameter that is less than the second opening diameter. The cap is placed over the third region and configured to hold the stepped pin within the first face opening.

An advantage of the present invention is that it allows for an offset orthopaedic reamer that can have a longer offset without increasing the length of the joints.

Another advantage is the reamer head can spin on an axis that is parallel to the axis of the rotary driver.

Yet another advantage is the rotating pins allow for a more even distribution of friction throughout the reamer handle, decreasing wear on each individual component.

BRIEF DESCRIPTION OF THE DRAWINGS

The above-mentioned and other features and advantages of this invention, and the manner of attaining them, will become more apparent and the invention will be better understood by reference to the following description of embodiments of the invention taken in conjunction with the accompanying drawings, wherein.

Corresponding reference characters indicate corresponding parts throughout the several views. The exemplifications set out herein illustrate embodiments of the invention and such exemplifications are not to be construed as limiting the scope of the invention in any manner.

DETAILED DESCRIPTION OF THE INVENTION

Figure 1:
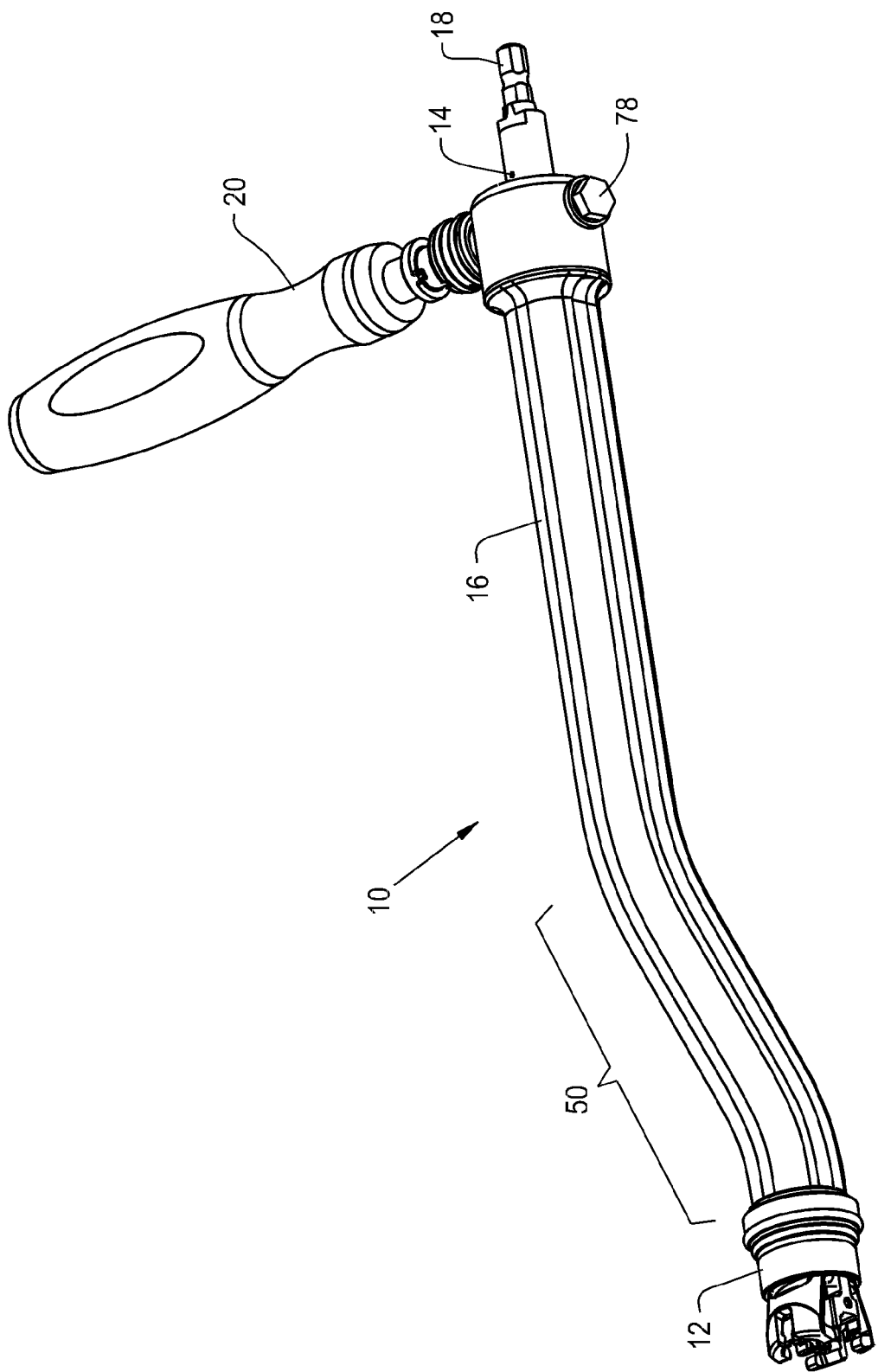
FIG. 1 is a perspective view of an orthopaedic reamer handle according to the present invention.

Referring now to the drawings, and more particularly to FIG. 1, there is shown an assembled orthopaedic reamer handle 10 which generally includes a reamer portion 12, a driver portion 14 connected to the reamer portion 12 and a casing 16 placed over a drive train (not shown) that connects the reamer portion 12 to the driver portion 14. The reamer portion 12 is configured to transmit torque to a reamer head (not shown), which will be used in an orthopaedic procedure. The driver portion 14 has a shank 18 that connects to a rotary driver, such as a drill, that provides torque to the driver portion 14, through the drive train to the reamer portion 12, and finally to the reamer head. The torque transmitted from the driver portion 14 to the reamer portion 12 will spin the reamer head, allowing for diseased bone and cartilage to be removed during the procedure. The reamer portion 12 and driver portion 14 can be constructed from any material and in any manner suitable for the reamer head and rotary driver being used. A gripping portion 20 is attached to the handle 10 between the shank 18 and casing 16 to provide a gripping surface for a user to hold while performing the orthopaedic reaming procedure.

Figure 2:
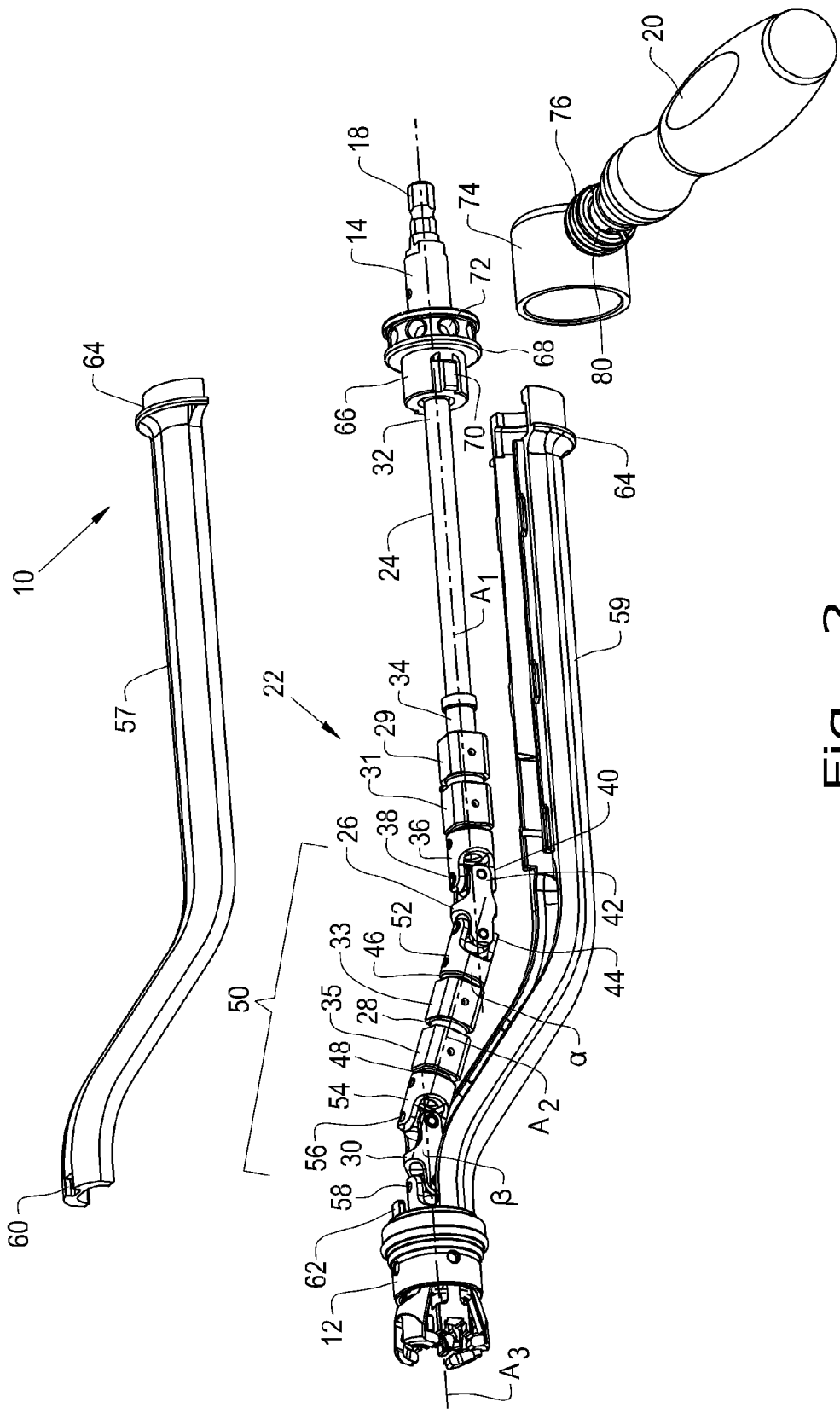
FIG. 2 is an exploded view of the orthopaedic reamer handle shown in FIG. 1.

Referring now to FIG. 2, the orthopaedic reamer handle 10 is shown in a disassembled state. A drive train 22 can be seen that includes a first drive shaft 24 connected to the driver portion 14, a first intermediate connector 26 connected to the first drive shaft 24, an offsetting member (shown as a pair of interconnecting members 29 and 31) 28 connected to the first intermediate connector 26, and a second intermediate connector 30 connected to the offsetting member 28 and the reamer portion 12. The first drive shaft 24 can have a first end 32 that connects to the driver portion 14 and a second end 34 that connects to the first intermediate connector 26. The first end 32 can connect to the driver portion 14 in any suitable way that allows for efficient transmission of torque, such as by adhesive bonding or a friction fit. The first drive shaft 24 could also be formed as one piece including the driver portion 14, in which case the first end 32 would refer to the portion of the first drive shaft 24 that is adjacent to the shank 18. Similarly, the second end 34 can connect to the first intermediate connector 26 directly or, as shown, using a first connector 36 connected to a pair of interconnecting members 33 and 35. As can be seen, interconnecting member 33 is connected to the second end 34 and interconnecting member 35 is connected to the first connector 36, with interconnecting members 33 and 35 connected together. Interconnecting member 33 can have a threaded opening (not shown) that interacts with a threaded protrusion (not shown) of interconnecting member 35, allowing for the interconnecting members 33, 35 to connect together. The first connector 36 can be a U-shaped connector with a first ear 38 and a second ear 40 that connect to the first intermediate connector 26, which is an H-shaped connector having a first intermediate end 42 connected to the second end 34 (through the first connector 36 and interconnecting members 33 and 35) and a second intermediate end 44 that connects to the offsetting member 28. The first connector 36 can be connected to the second end 34, as shown, or be formed as a part of the first drive shaft 24. The first drive shaft 24 defines a first axis A1, which can be the axis that torque generated by the rotary driver rotates about. The first intermediate connector 26 can connect to the first connector 36 along the first axis A1 or could connect at an angle relative to the first axis A1 if desired. The length of the first drive shaft 22 can be adjusted as desired to give the reamer handle 10 a longer or shorter length along the first axis A1.

The offsetting member 28 connects to the second intermediate end 44 at a third end 46 and has a fourth end 48 that connects to the second intermediate connector 30. The offsetting member 28, as shown in FIG. 2, consists of a pair of interconnecting members 29 and 31 that are connected together. If desired, a lengthener could be placed between the interconnecting members 29 and 31 to increase the length of the offsetting member 28. During operation, the offsetting member 28 defines a second axis A2 that is the longitudinal axis of the offsetting member 28. The offsetting member 28 connects to the second intermediate end 44 such that the second axis A2 creates an offset angle α relative to the first axis A1, which allows for an offset 50 to be created in the reamer handle 10. Offset angle α can be varied to adjust the geometry of the offset 50 in any desired fashion, but acute angles ranging between 15° and 60° have been found to be a clinically applicable range for offset angle α. If the first intermediate connector 26 is aligned with the first axis A1, offset angle α will be created as the angle at which the offsetting member 28 connects to the first intermediate connector 26 relative to the first axis A1. If the first intermediate connector 26 is connected to the first drive shaft 22 at an angle relative to the first axis A1, offset angle α will be the sum of the angles that the first intermediate connector 26 and offsetting member 28 create relative to the first axis A1 when connected. The length of the offsetting member 28 can be varied to create a longer offset 50, which can be beneficial in surgery. A longer offset 50 allows for reamer head access to a patient's joint that is farther away from the rotary driver outside the patient. The offsetting member 28 can include a second connector 52 attached to the third end 46 and a third connector 54 attached to the fourth end 48. The second connector 52 and third connector 54 can be configured similarly to the first connector 36, as U-shaped connectors, or as any other connector that is capable of transferring torque. The second connector 52 and third connector 54 can also be formed as an integral part of the offsetting member 28 at the third end 46 and fourth end 48, respectively.

Figure 3:
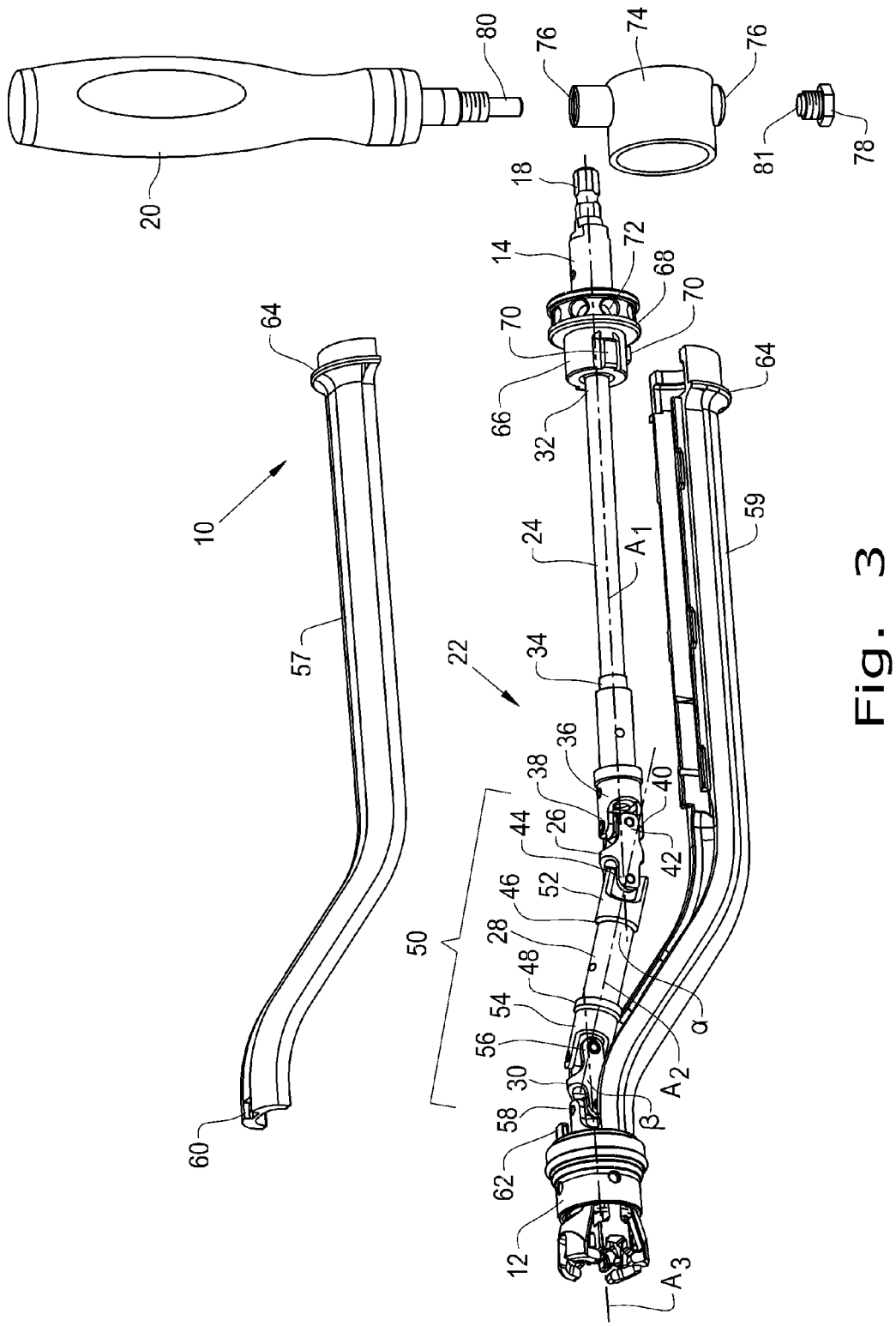
FIG. 3 is a perspective view of another orthopaedic reamer handle according to the present invention.

FIG. 3 shows another embodiment of the drive train 22 in which the offsetting member 28 is a second drive shaft. The second drive shaft 28 performs essentially the same basic function as the interconnecting members 33 and 35. The second drive shaft 28 can also be connected to interconnecting members 33 and 35 to act as a spacer between the interconnecting members 33 and 35. As used throughout the application, the second drive shaft 28 and pair of interconnecting members 33 and 35 can interchangeably be referred to as the offsetting member 28.

The second intermediate connector 30 is connected to the fourth end 48 at a third intermediate end 56 and the reamer portion 12 at a fourth intermediate end 58. The second intermediate connector 30 can be a separate component from the reamer portion 12, as shown, or could be part of the reamer portion 12. The second intermediate connector 30 is connected to the offsetting member 28 at a drive angle β relative to the second axis A2. Drive angle β can be chosen to be the corresponding angle of offset angle α, so that reamer portion 12 defines a third axis A3 that is parallel to the first axis A1. Such a configuration allows a user to approximate the angular position of the reamer head, if it isn't visible, using the rotary driver as a reference. Drive angle β can also be chosen such that the third axis A3 is not parallel to the first axis A1, if desired. If the second intermediate connector 30 is a separate component from the reamer portion 12, it can be an H-shaped connector, as shown, that connects to the third connector 54 and the reamer portion 12. The components of the drive train 22 can be made of any suitable material for transmitting torque from the rotary driver to the reamer head, e.g., stainless steel, aluminum, titanium, polymers.

As shown in FIG. 1, a casing 16 covers the drive train 22 between the reamer portion 12 and the driver portion 14. FIG. 2 shows the casing 16 in its disassembled state, which allows for cleaning of the reamer handle 10 and its components. The casing 16 includes a first half 57 and a second half 59, which surround the drive train 22. A groove 60 is formed at one end on the first half 57 and the second half 59 that is sized to allow for a tab 62 formed on the reamer portion 12 to rest within the groove 60. The tab 62 can tightly fit within the groove 60 to allow for a more secure connection. Semi-circular portions 64 can be formed at the other end of the first half 57 and the second half 59 to cover a connecting portion 66 of the reamer handle 10, where the first half 57 and the second half 59 will connect. The connecting portion 66 can have a stepped rim 68 and protrusions 70 formed thereon, as well as multiple openings 72. Once the first half 57 and second half 59 are placed over the connection portion 66, a locking ring 74 is placed over the first half 57, second half 59 and connecting portion 66 to keep the casing 16 together. The locking ring 74 can have threaded holes 76. The gripping portion 20 and a locking screw 78 have corresponding threading to the threaded holes 76 and, when inserted, keep the locking ring 74 connected to the connecting portion 66 and first half 57 and second half 59. The gripping portion 20 and locking screw 78 can also have unthreaded ends 80 that fit within the openings 72 formed in the connecting portion 66. The components of the casing 16 can be formed of any suitable material for use in surgery and holding the components of the reamer handle 10 together, such as stainless steel.

Figure 4:
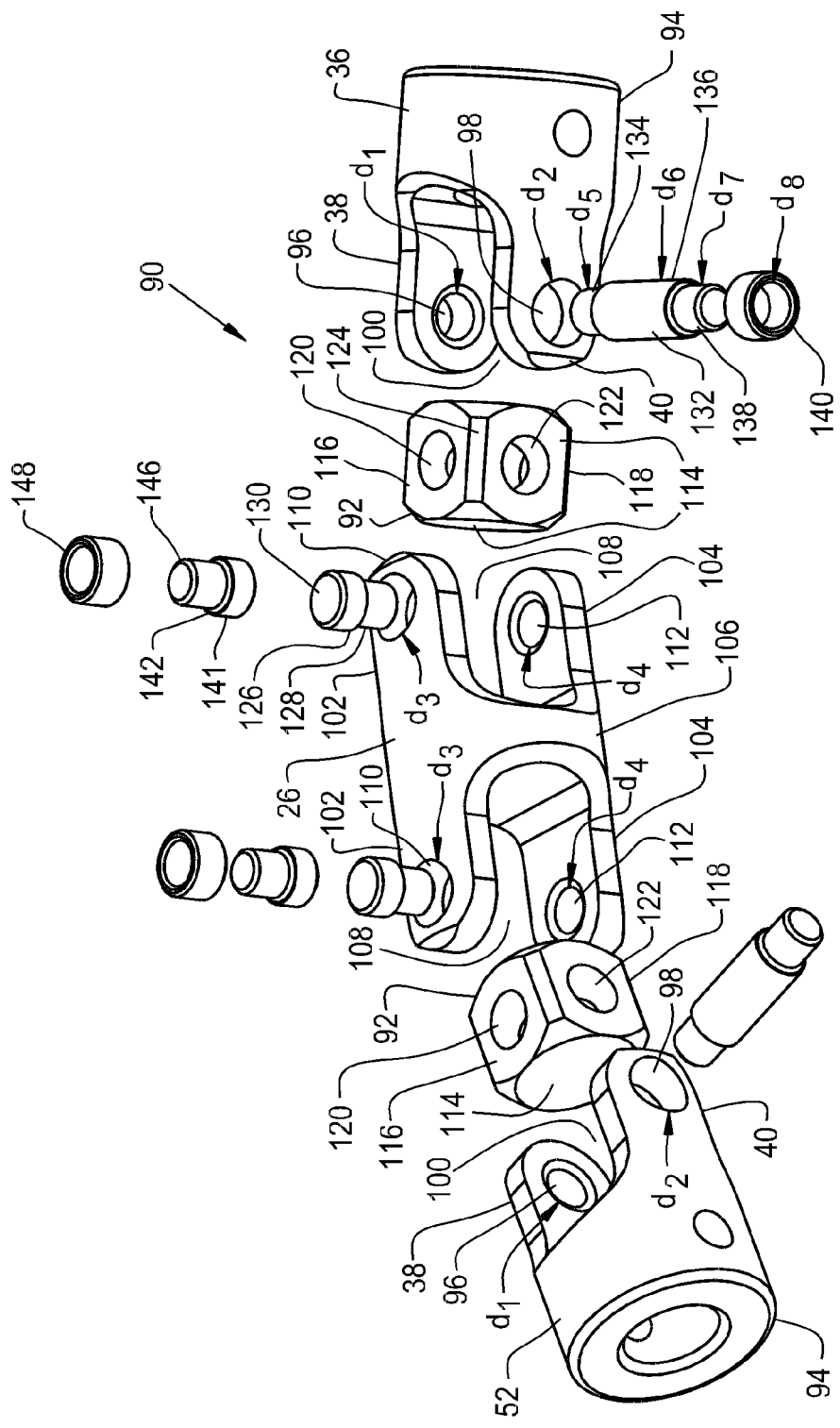
FIG. 4 is an exploded view of a joint according to the present invention.

Referring now to FIG. 4, an exploded view of a joint 90 used in the drive train 22 of FIG. 2 is shown. The joint 90 can include the first connector 36, the first intermediate connector 26 and the second connector 52 held together by joining members 92, or can be formed by one of the connectors 36, 52 and the first intermediate connector 26. First connector 36 and second connector 52 are U-shaped connectors each having a first ear 38 and a second ear 40 connected at a cylindrical base 94, with a first pin opening 96 formed on the first ear 38 and a second pin opening 98 formed on the second ear 40. Gaps 100 are formed between the first ear 38 and second ear 40 of each connector 36, 52, with the joining members 92 being placed within the gaps 100. The first pin opening 96 defines a first opening diameter d1 and the second pin opening 98 defines a second opening diameter d2. The ears 38, 40 are shown as being parallel to one another, but they could also be angled relative to one another if desired. The first connector 36 can be formed of any suitable material such as stainless steel or a wear-resistant polymer.

The first intermediate connector 26 is connected to the first connector 36 as part of the joint 90. As shown in FIG. 4, the first intermediate connector 26 is an H-shaped connector having a pair of opposed third ears 102 and a pair of opposed fourth ears 104 connected together at a base 106 with a gap 108 in between the respective third ears 102 and fourth ears 104. Each third ear 102 has a third pin opening 110 defining a third opening diameter d3 formed through and each fourth ear 104 has a fourth pin opening 112 defining a fourth opening diameter d4 formed through. The H-shaped connector 26 is, for all intents and purposes, a pair of U-shaped connectors fused together at the base 106. As such, the third ears 102 can be parallel or angled relative to each other, the fourth ears 104 can be parallel or angled relative to each other, and the third ears 102 can be parallel or angled relative to the fourth ears 104. The lengths and widths of the third ears 102, fourth ears 104 and base 106 can also be altered to give the joint 90 a desired geometry. The first intermediate connector 26 can be formed of any suitable material such as stainless steel or a wear-resistant polymer.

The joining members 92 can be formed as cube shaped blocks with faces 114. Opposed faces 116 and 118 have a first face opening 120 formed between the faces 116, 118, providing a complete opening through the joining members 92. At least one other face 114 can have a second face opening 122 formed through that extends through the joining member 92 to the first face opening 120 within the joining member 92. One or more facets 124 can be formed between two or more faces 114 of the joining member 92, if desired. The facet(s) 124 can provide a more predictable and even wear surface than a sharp edge if the joining member 92 rubs against any of the connectors. The joining members 92 can be made of any suitable material such as stainless steel or a wear-resistant polymer.

To form joint 90, a stepped half pin 126 is placed through the fourth pin opening(s) 112 of the first intermediate connector 26. The stepped half pin 126 has a small diameter region 128 with a diameter that is smaller than the fourth opening diameter d4, and a large diameter region 130 with a diameter that is larger than the fourth opening diameter d4. The joining member 92 is then placed within gap 108, either abutting against the large diameter region 130 or having the large diameter region 130 resting within an opening (not shown) formed in the joining member 92. The first connector 36 (or second connector 52) is then placed over the joining member 92 so that the joining member 92 rests within gap 100. A stepped pin 132 is then placed within the first pin opening 92, first face opening 120 and second pin opening 94 to connect the joining member 92 to the first connector 36. The stepped pin 132 has a first region 134 with a first pin diameter d5, a second region 136 with a second pin diameter d6 and a third region 138 with a third pin diameter d7. First pin diameter d5 is less than the first opening diameter d1 so that the first region 134 rests at least partially within the first pin opening 92. Second pin diameter d6 is greater than the first opening diameter d1 but less than second opening diameter d2, so that the second region 136 can slide through the second pin opening 94 but will not pass through the first pin opening 92, instead abutting against the first pin opening 92. The second region 136 therefore forms a shoulder for the stepped pin 132 that abuts against the first ear 38 and second ear 40. Third pin diameter d7 is less than the second opening diameter d2 so that the third region 138 will rest at least partially within the second pin opening 94. A cap 140 is placed over the third region 138 within the second pin opening 94 to hold the stepped pin 132 within the first pin opening 92, first face opening 120 and second pin opening 94. The cap 140 has a cap diameter d8 that can be slightly larger than the second opening diameter d2, so that the cap 140 can be press fit into the second pin opening 94, or the cap 140 can be held within the second pin opening 94 in any other suitable way to keep the joining member 92 connected to the first connector 36. It's also contemplated that the cap 140 could be a part of the stepped pin 132 itself, either as a region that is press fit into the second pin opening 94 or that is expanded to be greater than the second opening diameter d2 once the stepped pin 132 is properly placed. Wear-resistant polymers have been found to be useful materials for forming the cap 140.

Once the stepped pin 132 is placed and holding the joining member 92 to the first connector 36, another stepped half pin 142 can be placed in the third pin opening 110. The stepped half pin 142 can have a large diameter region 144 and a small diameter region 146, similarly to the stepped half pin 126. The large diameter region 144 can fit and rest within the second face opening 122 and the small diameter region 146 can rest within the third pin opening 110. Once the stepped half pin 142 is placed, a second cap 148 is placed over the small diameter region 146 in the third pin opening 110, securing the stepped half pin 142 and completing the joint 90. Using the stepped half pins 126 and 142 and stepped pin 132 with caps 140 and 148 in the joint 90 allows for the pins 126, 132, 142 to rotate while torque is being transmitted through the drive train 22. The pins 126, 132, 142 rotating allows for friction to be more evenly distributed throughout the drive train 22, reducing the wear that the individual components experience and prolonging the effective life of the drive train 22 before needing repair or replacement. While the previous discussion focused on the joint 90 between the first connector 36 and the first intermediate connector 26, joint 90 can be similarly utilized to join any components within the drive train 22 or to connect the drive train 22 to the reamer portion 12 or driver portion 14.

Figure 5:
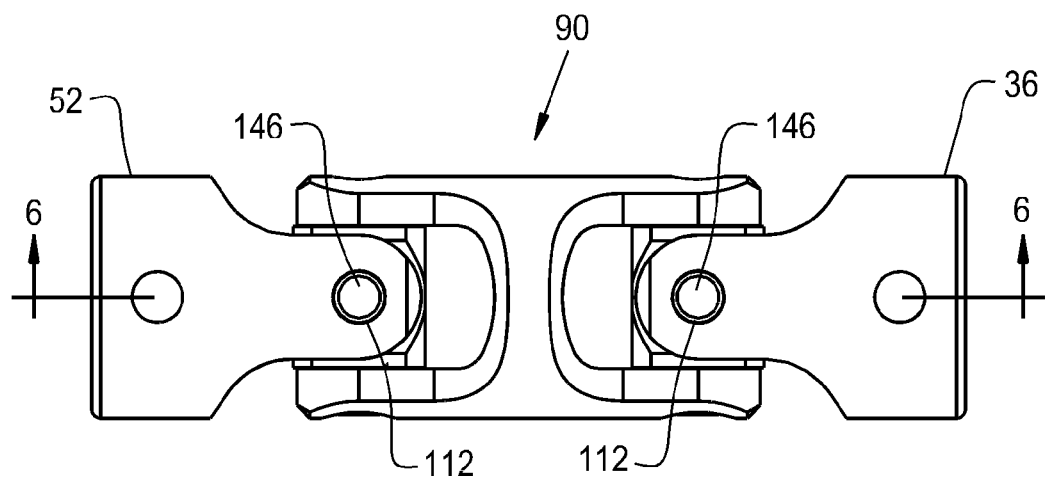
FIG. 5 is a perspective view of a joint according to the present invention.
Figure 6:
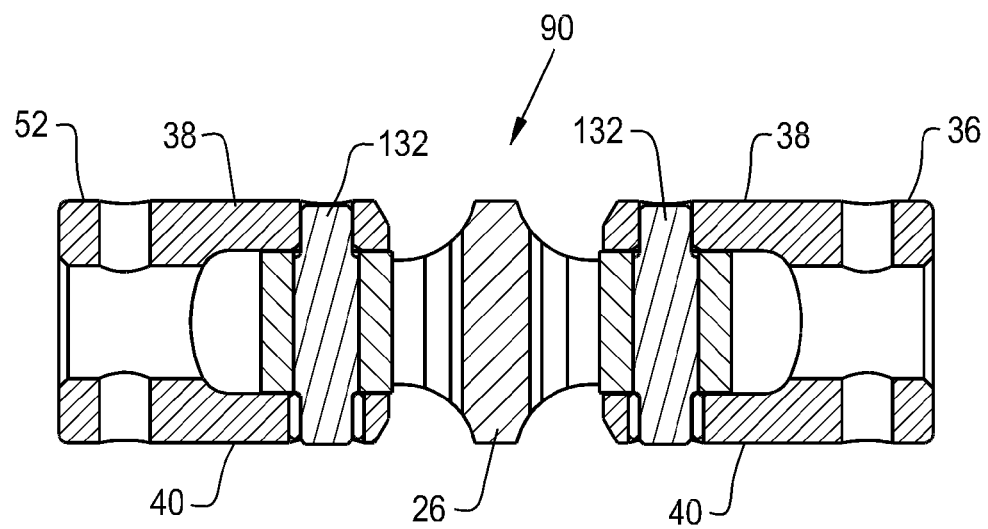
FIG. 6 is a cross-sectional view along line E-E shown in FIG. 5.
Figure 7:
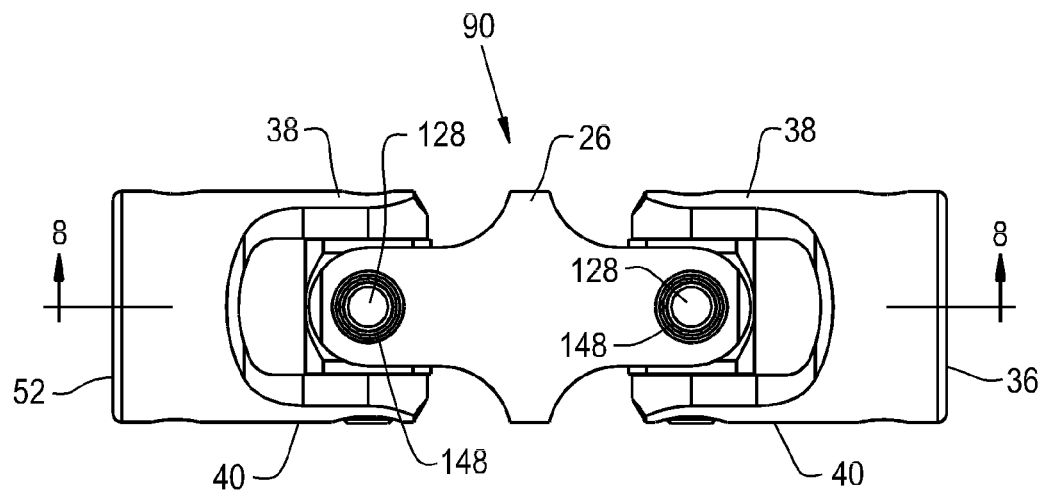
FIG. 7 is another perspective view of the joint shown in FIG. 5.
Figure 8:
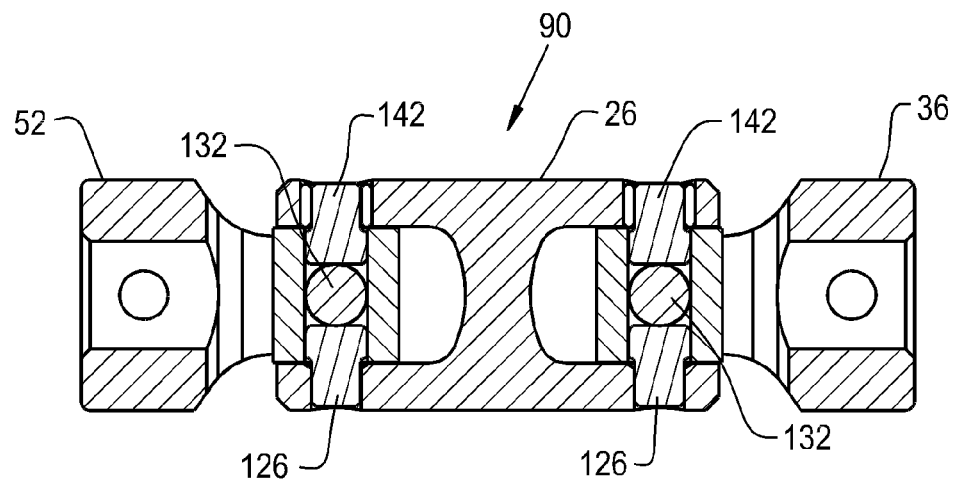
FIG. 8 is a cross-sectional view along line D-D shown in FIG. 7.

FIGS. 5-8 show perspective views of the joint 90 when it is fully assembled. As can be seen in FIG. 5, the small diameter regions 146 of stepped half pin 126 are held in the fourth pin openings 112 and restrict movement of the joining members 92. FIG. 6 shows a sectional view of the joint 90 along line E-E in FIG. 5 and shows the stepped pins 132 residing within the joining members 92 and the connectors 36, 52. FIG. 7 shows the small diameter regions 128 of the stepped half pins 126 being held within the third pin openings 110 by caps 148, restricting movement of the joining members 92. FIG. 8 shows the stepped half pins 126, 142 pressing on the stepped pin 132 to keep the connectors 36, 52, joining members 92 and first intermediate connector 26 together. While the joint 90 is shown as having pins residing within the connectors 36 and 52, joining member 92 and first intermediate connector 26, it is contemplated that stepped pin 132 and cap 140 would only reside within the joining member 92 and either one of the connectors 36 and 52 or the first intermediate connector 26. If the stepped pin 132 and cap 140 only reside within one of the connectors 36, 52 or the first intermediate connector 26, the other parts of the joint 90 could be connected together using another suitable method such as adhesion.

While this invention has been described with respect to at least one embodiment, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A joint for transmitting torque in an orthopaedic reamer handle, comprising:
    a first connector, said first connector including a first ear and a second ear connected to a base and separated by a first gap, said first ear having a first pin opening with a first opening diameter and said second ear having a second pin opening with a second opening diameter which is greater than said first opening diameter;
    a joining member placed within said first gap, said joining member having a pair of opposing faces with a first face opening formed therethrough;
    a second connector including a pair of ears pivotably connected to said joining member;
    a stepped pin placed within said first pin opening, said second pin opening and said first face opening, said stepped pin having a first region with a first pin diameter held within said first pin opening, a second region with a second pin diameter held within said first face opening and a third region with a third pin diameter held within said second pin opening, said first pin diameter being less than said first opening diameter, said second pin diameter being greater than said first opening diameter and less than said second opening diameter and said third pin diameter being less than said second opening diameter, said respective pin diameters of said first region, said second region, and said third region allowing axial sliding into respective openings of said first ear, said second ear, and said joining member such that said second region of said pin abuts said first ear when said first pin opening, said second pin opening, and said first face opening are aligned; and
    a cap engaging said third region and fixedly held within said second pin opening.

2. The joint according to claim 1, wherein said pair of ears of said second connector includes a third ear having a third pin opening formed through and a fourth ear having a fourth pin opening formed through.

3. The joint according to claim 2, wherein said joining member has a third face with a second face opening formed thereon and a fourth face with a third face opening formed thereon.

4. The joint according to claim 3, further including a first pin connecting said second connector to said joining member through said third pin opening and said second face opening and a second pin connecting said second connector to said joining member through said fourth pin opening and said third face opening.

5. The joint according to claim 4, wherein said joining member has a substantially cubed shape.

6. The joint according to claim 5, wherein said joining member has at least one facet formed between at least two faces of said joining member.

* * * * *